United States Patent
Bruna

(10) Patent No.: US 6,234,168 B1
(45) Date of Patent: May 22, 2001

(54) DOSIMETER

(75) Inventor: Pascal Bruna, Rouen (FR)

(73) Assignee: Valois S.A., Le Neubourg (FR)

( * ) Notice: Subject to any disclaimer, the term of this patent is extended or adjusted under 35 U.S.C. 154(b) by 0 days.

(21) Appl. No.: 09/214,491

(22) PCT Filed: Jun. 26, 1997

(86) PCT No.: PCT/FR97/01151

§ 371 Date: May 4, 1999

§ 102(e) Date: May 4, 1999

(87) PCT Pub. No.: WO98/01822

PCT Pub. Date: Jan. 15, 1998

(30) Foreign Application Priority Data

Jul. 5, 1996 (FR) .................................................. 96 08381

(51) Int. Cl.[7] .................................................. A61M 15/00
(52) U.S. Cl. .................. 128/203.12; 239/71; 222/36; 222/28; 417/435; 415/11; 128/200.23
(58) Field of Search .................. 128/200.23, 203.12; 239/71; 222/36, 28; 417/435; 415/11

(56) References Cited

U.S. PATENT DOCUMENTS

| | | | |
|---|---|---|---|
| 4,817,822 | * 4/1989 | Rand et al. | 222/38 |
| 5,349,945 | * 9/1994 | Wass et al. | 128/200.23 |
| 5,392,768 | * 2/1995 | Johansson et al. | 128/200.14 |
| 5,611,444 | * 3/1997 | Garby et al. | 215/230 |
| 5,740,792 | * 4/1998 | Ashley et al. | 128/203.15 |

FOREIGN PATENT DOCUMENTS

| | | |
|---|---|---|
| 684 047 | 11/1995 | (WO) . |
| WO 95/34874 | * 12/1995 | (WO) . |
| WO 96/16687 | 6/1996 | (WO) . |

* cited by examiner

*Primary Examiner*—Glenn K. Dawson
*Assistant Examiner*—Mital Patel
(74) *Attorney, Agent, or Firm*—Sughrue, Mion, Zinn, Macpeak & Seas, PLLC

(57) ABSTRACT

An apparatus for measuring doses of dispensed products includes a first metering ring (20) mounted to rotate 5 around a rotation axis (1), and drive means (10) that drives the first metering ring to rotate around an axis (1). The drive means (10) is actuated each time the dispenser is actuated. The apparatus also has interlocking means (15, 22) that engage the drive means (10) with the first metering ring (20) after the dispenser has been actuated a predetermined number of times. The first metering ring (20) is driven to rotate once it is engaged with the drive means (10). The apparatus only counts the doses of dispensed product after the dispenser has been actuated a predetermined number of times.

10 Claims, 3 Drawing Sheets

DOSIMETER

BACKGROUND OF THE INVENTION

1. Field of the Invention

The present invention relates to an apparatus for measuring doses of products dispensed by a fluid or powdery product dispenser. In particular, the present invention relates to an apparatus that allows for one or several no-load operations that are not counted.

2. Description of the Related Art

Document WO 95/34874 discloses a dosimeter that functions satisfactorily.

When using dispensing valves and also certain pumps it may, however, be preferable to actuate the apparatus once or twice before the first use under load. However, the apparatus disclosed in WO 95/34874 measures a dose each time the dispenser is actuated. It is therefore impossible to effectuate one or several no-load operations for example in order to prime the pump or to carry out trial operations before use. It is also impossible to guarantee dispensing of a complete dose at the first actuation.

SUMMARY OF THE INVENTION

The aim of the present invention is therefore to build a system for measuring doses of products dispensed by a fluid or powdery product dispenser that does not have the above-mentioned disadvantage.

The aim of the present invention is therefore to provide a dosimeter of this type that only counts the doses that have been dispensed after the dispenser has been actuated a predetermined number of times.

The aim of the present invention is also to provide an apparatus of this type that is simple and inexpensive to produce and to assemble.

It is also an aim of the present invention to provide an apparatus of this type that can be used to measure the doses dispensed by a dispensing valve.

Another aim of the present invention is to provide a dosimeter of this type that is capable of being simply and inexpensively fitted to various dispensers, particularly to dispensers with various actuating device travels.

The object of the present invention is therefore an apparatus for measuring doses of products dispensed by a fluid or powdery product dispenser, the measuring apparatus comprising:

a first metering ring mounted to rotate about a rotation axis, and drive means capable of co-operating with the first metering ring in order to drive it in rotation about the axis, the drive means being actuated each time the dispenser is actuated, the apparatus comprising interlocking means for engaging the drive means with the first metering ring after the dispenser has been actuated a predetermined number of times, the first metering ring being driven to rotate only as from when it is engaged with the drive means, such that the measuring apparatus only counts the doses that have been dispensed after the dispenser has been actuated the predetermined number of times.

Preferably, the drive means comprise a drive wheel that is mounted to rotate around the rotation axis of said first metering ring near to which the drive wheel is driven to rotate around the rotation axis each time the dispenser is actuated.

Advantageously, said interlocking means comprise a foot that is an integrated part of said drive wheel. The foot is more or less parallel to said rotation axis and co-operates with a slot provided in said first metering ring, said slot coming to bear on an end surface of said slot after the dispenser has been actuated said number of predetermined times.

Advantageously, said slot lies in the arc of a circle in said first metering ring. Each time the dispenser is actuated the drive wheel is driven to rotate around said rotation axis, said foot being simultaneously displaced in said slot without causing the first metering ring to rotate, eventually resulting in said foot coming to bear on the radial end surface of the slot. Any subsequent actions of the dispenser bring the foot of the drive wheel to drive said first metering ring to rotate around said rotation axis in order to count the doses of dispensed product. The length of the slot thus constitutes said predetermined number of times that the dispenser is actuated during which the metering ring does not turn.

In particular, said first metering ring and said drive wheel each comprise a respective anti-return device that prevents said first ring and said drive wheel from rotating in the opposite directions.

Preferably, the dispenser comprises an actuating device capable of being displaced between a rest position and an actuating position such that every time the dispenser is actuated said actuating device operates in conjunction with said drive wheel in order to rotate the drive wheel through a predetermined angle around said rotation axis.

Advantageously, the actuating device is displaced in a direction parallel to the rotation axis of said drive wheel and to said first metering ring.

Advantageously, said drive wheel comprises two rows of indentations that are arranged around the circumference and that project radially outwards. The indentations of the first row of indentations have a first oblique surface that operates in conjunction with the actuating device when the device is displaced from the rest position to the actuating position. The indentations of the second row have a second oblique surface that operates in conjunction with the actuating device when the device is displaced from the actuating position to the rest position, such that the drive wheel rotates through said predetermined angle during an actuating cycle of the actuating device.

In particular, said dispenser comprises a dispensing valve that is actuated by a push-button, said push-button including said actuating device such that when the user depresses the push-button to obtain a dose the drive wheel rotates through a section of said predetermined angle and when the push-button is brought back to its initial position said drive wheel rotates through the remainder of the predetermined angle.

The apparatus may also comprise a second metering ring mounted to rotate around said rotation axis and that is actuated to rotate by the first metering ring each time that said first metering ring has completed a 360° rotation around said rotation axis. In this example, the co-operation between the first metering ring and the second metering ring may be identical to that described in document WO 95/34874.

BRIEF DESCRIPTION OF THE DRAWINGS

Other characteristics and advantages of the present invention will be shown in the following detailed description given as a non-limitative example in reference to the attached drawings in which.

DETAILED DESCRIPTION OF THE INVENTION

In reference to FIGS. 1, 2, 5 and 6, the apparatus for measuring doses dispensed by a fluid or powdery product dispenser of the invention is the same type as that of document WO 95/34874. Therefore, operation of this apparatus will only be briefly described hereafter and the above-mentioned document is included here as a reference for the general operation of the apparatus for measuring and particularly for the effective counting of doses of dispensed product.

Figure 1:
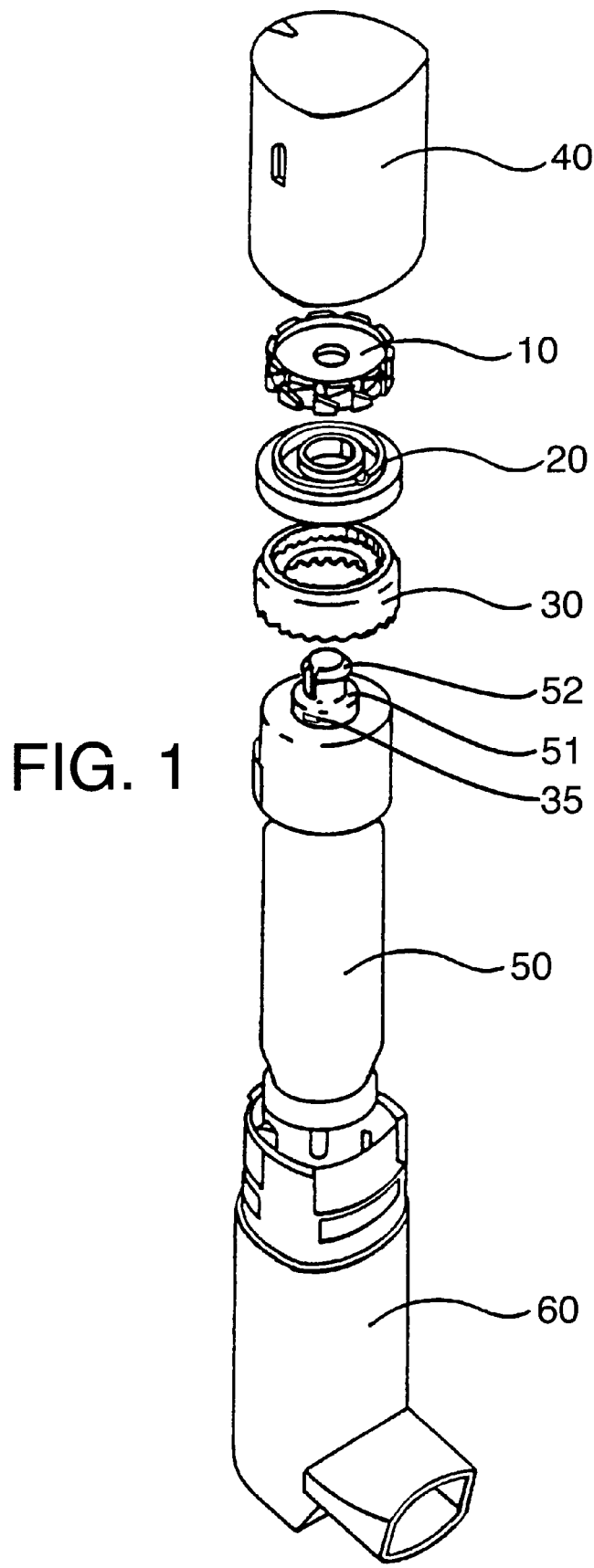
FIG. 1 is a schematic exploded view of a measuring apparatus according to the invention.
Figure 5:
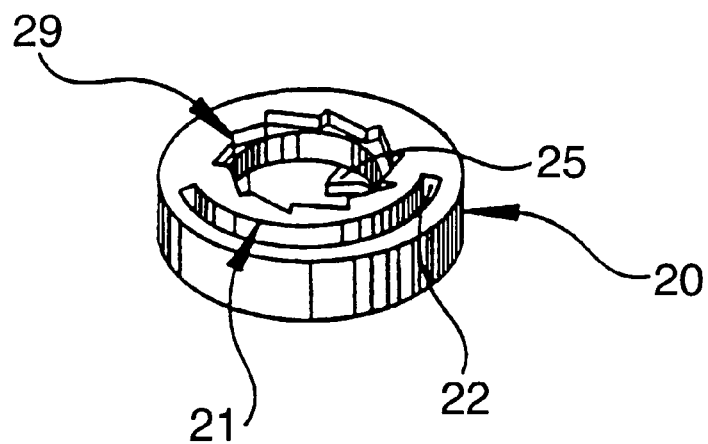
FIG. 5 is a schematic perspective view of the first metering ring according to the present invention.
Figure 6:
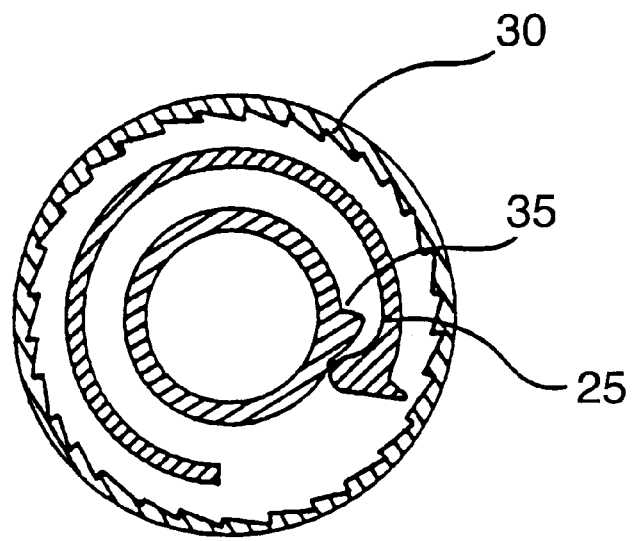
FIG. 6 is a schematic horizontal section showing the co-operation between the first metering ring and the second metering ring.

As shown in FIGS. 1, 2, 5 and 6, the apparatus for measuring doses comprises at least one first metering ring 20 and one or more other metering rings. In particular, the present apparatus comprises a second metering ring 30. The dispenser actuates the first metering ring 20 to be driven to rotate around its rotation axis 1. As shown in FIG. 6, the second metering ring 30 is driven to rotate by said first metering ring 20 when said first metering ring has completely rotated around its axis 1. The first and second metering rings 20, 30 are particularly suited to counting individual units and groups of ten respectively. The first metering ring 20 advantageously comprises a flexible foot 25 that is capable of operating in conjunction with a fixed cam 35 each time said first ring has completed a rotation around rotation axis 1. As shown in FIG. 1, for example, the fixed cam 35 may be provided on a shoulder 51 of the dispensing valve 50. When foot 25 operates in conjunction with cam 35 said foot is forced into contact with said second metering ring 30 in order to cause said second metering ring also to rotate around said axis 1. The first and second metering rings can, clearly, comprise anti-return systems in order to avoid these metering rings rotating in an opposite direction to that which is imposed by the actuation of the dispenser. In particular, the first metering ring 20 can comprise internal toothing 29 that co-operates with a catch that is fixed relative to the rotation axis 1. The principle of the apparatus for measuring is therefore the same as that disclosed in document WO 95/34874.

However, in this apparatus the first metering ring 20 is driven to rotate each time the dispenser is actuated. It is therefore impossible in the apparatus of the prior art for the dispenser to effectuate no-load i.e. uncounted operations before beginning to measure the first dose.

Figure 2:
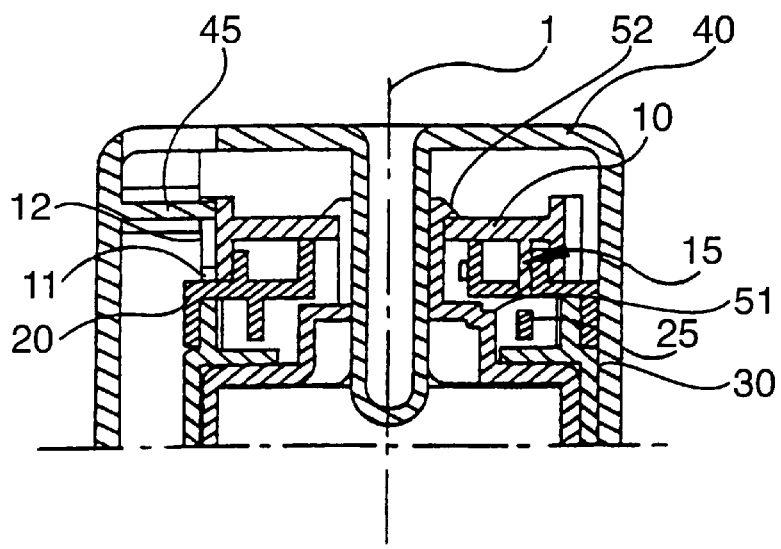
FIG. 2 is a schematic vertical section through a measuring apparatus according to the invention

The present invention therefore concerns a measuring apparatus that enables the dispenser to be actuated a predetermined number of times before the apparatus for measuring begins to count the doses dispensed. Whereas in the apparatus of the prior art the first metering ring is driven to rotate each time the dispenser is actuated, the present invention enables the first metering ring 20 to be driven to rotate, and therefore to count the doses dispensed, only after the dispenser has been actuated a predetermined number of times. In order to do this, the present invention provides for the first metering ring 20 to be driven by driving means 10, advantageously in the form of a drive wheel, that is mounted to rotate around the same rotation axis 1. As shown in FIGS. 1 and 2, the dispensing valve 50 includes an assembling flange 52 that supports the drive wheel 10 in a fixed axial position and allows for rotation.

This drive wheel 10 is driven to rotate around axis 1 each time the dispenser is actuated but it only co-operates with first metering ring 20 to drive said metering ring to rotate around axis 1 as from said predetermined number of times the dispenser is actuated. Therefore, this apparatus includes interlocking means to engage drive wheel 10 with first metering ring 20 after the predetermined number of times the dispenser is actuated. These interlocking means advantageously comprise a foot 15 that is fastened to or is an integrated part of drive wheel 10 and that operates in conjunction with a suitable slot 21 provided in first metering ring 20. In reference to FIGS. 2 and 3, foot 15 is shown to be an integrated part of said drive wheel 10 and lies more or less parallel to said rotation axis 1. FIG. 5 also shows that said slot 21 provided in the said first metering ring 20 advantageously lies in the arc of a circle in said first metering ring 20. Therefore, each time the dispenser is actuated, drive wheel 10 is driven to rotate, said foot 15 being simultaneously displaced in said slot 21 without the first metering ring 20 being caused to rotate. It is only when foot 15 comes to bear on radial end surface 22 of slot 21 that, during a subsequent operation of the dispenser, foot 15 of drive wheel 10 drives first metering ring 20 to rotate around rotation axis 1 to begin measuring dispensed doses. Consequently, the length of said slot 21 determines the predetermined number of times that the dispenser is actuated during which first metering ring 20 does not rotate and during which the apparatus for measuring does not therefore count the doses of product dispensed.

The drive wheel 10 can clearly also comprise an anti-return device identical to that in FIG. 5 for first metering ring 20 i.e. internal toothing that co-operates in conjunction with a system of catches fixed relative to rotation axis 1. Thus, drive wheel 10 and first metering ring 20 are only capable of rotating in the direction that is imposed by the operation of the measuring apparatus.

The drive wheel 10 is driven to rotate around axis 1 each time the dispenser is actuated. This drive wheel 10 may be fitted to any apparatus for measuring as disclosed in document WO 95/34874 and more generally to any measuring apparatus that is actuated by the dispenser operation.

One embodiment of the said drive wheel 10 will now be described with reference to FIGS. 1 to 4. This embodiment is particularly suited to a dosimeter that operates in a dispenser actuated by an actuating device and that is displaced in a direction parallel to the rotation axis 1 of the drive wheel 10 and of first metering ring 20.

In particular, the dispenser can comprise a dispensing valve 50 that is actuated by a push-button 40, said 40, said push-button 40 including an actuating device 45 in the form of a foot that lies radially in relation to rotation axis 1 of the apparatus for measuring, as shown in FIG. 2. The dispensing valve also comprises a mouth piece 60 through which the dose of product is expelled in the direction of the user. The dispensing valve 50 shown in FIG. 1 can clearly be replaced with any other type of dispensing device such as a pump.

Figure 3:
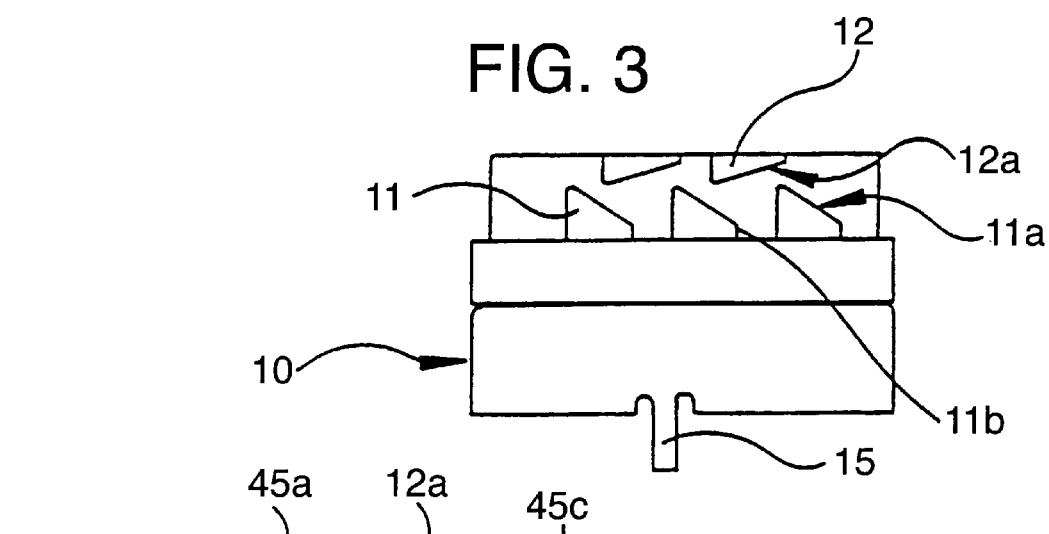
FIG. 3 is a schematic view of the drive wheel according to the invention.
Figure 4:
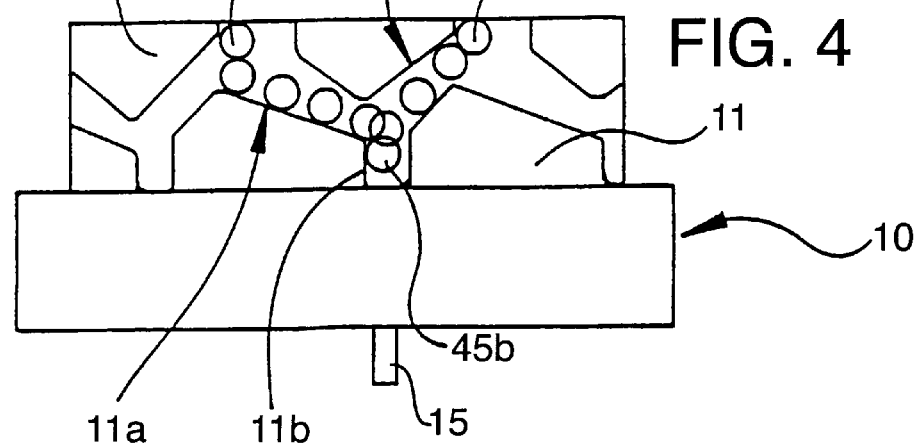
FIG. 4 is a schematic view of said drive wheel showing the co-operation between the driving device and said drive wheel during an actuating cycle of the dispenser.

In reference to FIGS. 1 and 2, push-button 40 is therefore capable of being displaced between a rest position and an actuating position. The push-button 40 includes an actuating device 45 that is also therefore capable of being displaced between an actuating position and a rest position. The actuating device 45 is such that each time the valve or the apparatus in general is actuated said actuating device co-operates with drive wheel 10 to rotate said drive wheel through a determined angle around rotation axis 1. In order to do this, drive wheel 10 advantageously comprises two rows of indentations 11 and 12 that are provided around the circumference of the drive wheel, as shown in FIGS. 3 and 4. Preferably, these indentations project outwards in order to work in conjunction with said actuating device 45. Advantageously, these indentations 11 of the first row of indentations have a first oblique surface 11a that co-operates with actuating device 45 when said actuating device is displaced from the rest position to the actuating position. The indentations 12 of the second row of indentations have a second oblique surface 12a that co-operates with actuating device 45 when said actuating device returns from the actuating position to the rest position. Consequently, said drive wheel 10 rotates through said determined angle during a complete actuating cycle of the actuating device 45. In particular, as shown in FIG. 3, the circumference of first oblique surface 11a of the first row of indentations is offset relative to the circumference of second oblique surface 12a of the second row of indentations 12. FIG. 4 shows schematically the successive positions of actuating device 45 during an actuating cycle of push-button 40. Thus when the push-button is still in the rest position, the actuating device is in position 45a. The user then depresses push-button 40 and actuating device 45 descends until it reaches first oblique surface 11a of a first indentation 11. From this stage onwards the continuation of the push-button displacement causes pressure to be forced on said indentation 11, said pressure comprising a non-vertical component such that drive wheel 10 is driven to rotate. When push-button 40 reaches the actuating position, actuating device 45 moves into the position referred to as 45b. At this stage, drive wheel 10 has only traveled through part of the determined rotation angle through which it rotates each time the dispenser is actuated. When the user releases pressure on push-button 40 after the dose is dispensed, said push-button 40 is brought back to the rest position, by means of a spring for example, and actuating device 45 is therefore brought vertically upwards until it makes contact with second oblique surface 12a of a second indentation 12. At this stage actuating device 45 applies compression force to indentation 12, said compression force also comprising a non-vertical component such that the drive wheel is again driven to rotate around the rotation axis. The oblique surfaces of first rows of indentations 11 and second rows of indentations 12 are oriented such that the two vertical components of compression force that are applied respectively to the two rows of indentations cause the drive wheel to rotate in the same direction of rotation. Therefore, when push-button 40 returns to the rest position after a complete actuating cycle of the dispenser, actuating device 45 moves into the position referred to as 45c and the drive wheel has effectuated a rotation through the determined angle around the rotation axis. Clearly, if the interlocking means i.e. foot 15 and slot 21 operate in conjunction, drive wheel 10 simultaneously causes first metering ring 20 to rotate and a dispensed dose is counted by the measuring apparatus. In this example, when the dispenser is actuated the rotation angle of first metering ring 20 is clearly the same as that of drive wheel 10.

It is particularly advantageous, as shown in FIGS. 3 and 4, that first oblique surface 11a of first row of indentations 11 is extended by a vertical section 11b. When actuating device 45 is displaced in this section it no longer applies compression force on first row of indentations 11 with a non-vertical component. This vertical section 11b is intended to enable push-button 40 to be brought to the actuating position. Therefore, drive wheel 10 of the present invention is suitable for any existing dispensing valves, whatever the actuating travel of the push-button. If the dispensing valve comprises a short actuating travel, the actuating device will not then be capable of reaching the bottom of section 11b when the push-button is actuated and will be displaced directly from the first oblique surface 11a onto the second oblique surface 12a. On the contrary, if the dispensing valve has a longer actuating travel, section 11b then compensates for the difference in travel and does not require the drive wheel to be modified for each different dispensing valve. This is also valid for pumps that also comprise various actuating travels according to the volume of doses dispensed. The apparatus of the invention may therefore be fitted to any type of existing pump or dispensing valve. The invention thus results in a major reduction in costs and enables easy manufacture and assembly.

The predetermined number of times that the dispenser is actuated during which the apparatus for measuring does not count i.e. the length of slot 21 provided in first metering ring 20, is determined in advance taking into account a certain number of operations that are preferably made before the product user actually dispenses the first dose for use. These no-load operations may, for example, require the apparatus to be actuated one or more times.

Even though the present invention has been described in relation to a dosimeter similar to that disclosed in document WO 95/34874, it is clearly suited to any type of measuring apparatus that is intended to measure a dose of product each time the dispenser is actuated. Similarly, even though the present invention has been particularly described in relation to a dispenser or actuating device applying parallel travel to the rotation axis of the apparatus for measuring, as in the example of a dispensing valve, the invention is clearly suitable for any type of dispenser, however it may be actuated.

What is claimed is:

1. An apparatus for measuring doses of products dispensed by a fluid or powdery product dispenser, said apparatus for measuring comprising:

a first metering ring (20) mounted to rotate around a rotation axis (1), and drive means (10) capable of co-operating with said first metering ring (20) to drive said metering ring to rotate around said axis (1), said drive means (10) being actuated each time the dispenser is actuated, characterized by the fact that said apparatus comprises interlocking means (15, 22) that are used to engage said drive means (10) with said first metering ring (20) after the dispenser has been actuated a predetermined number of times, said first metering ring (20) only being driven to rotate once it is engaged with said drive means (10), such that the apparatus for measuring only counts the doses of dispensed product after the dispenser has been actuated said predetermined number of times.

2. The apparatus of claim 1 wherein said drive means comprise a drive wheel (10) that is mounted to rotate around the rotation axis (1) of said first metering ring (20) near said first metering ring (20), said drive wheel (10) being driven to rotate around said rotation axis each time the dispenser is actuated.

3. The apparatus of claim 2 wherein said interlocking means comprise a foot (15) that is an integrated part of said drive wheel (10), said foot (15) being more or less parallel to said rotation axis (1) and operating in conjunction with a slot (21) that is provided in said first metering ring (20), said foot (15) coming to bear on an end surface (22) of said slot (21) after the dispenser has been actuated a predetermined number of times.

4. The apparatus of claim 3 wherein said slot (21) lies in the arc of a circle in said first metering ring (20), each time the dispenser is actuated to rotate said wheel (10) around said rotation axis (1), said foot (15) being simultaneously displaced in said slot (21) without causing said first metering ring (20) to rotate until said foot (15) comes to bear on a radial end surface (22) of said slot (21), any subsequent actions of the dispenser bringing said foot (15) of the drive wheel (10) to drive said first metering ring (20) to rotate around said rotation axis (1) in order to count the doses of dispensed product, the length of the slot thus constituting said predetermined number of times that the dispenser is actuated during which the metering ring (20) does not turn.

5. The apparatus of claim 2 wherein said first metering ring and said drive wheel do not rotate in opposite directions.

6. The apparatus of claim 2 wherein the dispenser comprises an actuating device (45) that is capable of being displaced between a rest position and an actuating position such that each time the dispenser is actuated said actuating device (45) operates in conjunction with said drive wheel (10) to rotate said drive wheel through a predetermined angle around said rotation axis.

7. The apparatus of claim 6 wherein said actuating device (45) is displaced in a direction parallel to the rotation axis (1) of said drive wheel (10) and of said first metering ring (20).

8. The apparatus of claim 7 wherein said drive wheel (10) comprises two rows of indentations (11, 12) that are arranged around the circumference and that project radially outwards, the indentations (11) of the first row of indentations have a first oblique surface (11a) that operates in conjunction with the actuating device (45) when the device is displaced from the rest position to the actuating position and the indentations (12) of the second row have a second oblique surface (12a) that operates in conjunction with the actuating device (45) when the device is displaced from actuating position to the rest position, such that the said drive wheel (10) rotates through said predetermined angle during an actuating cycle of the actuating device (45).

9. The apparatus of claim 8 wherein said dispenser comprises a dispensing valve (50) actuated by a push-button (40), said push-button (40) including said actuating device (45) such that when the user depresses push-button (40) to obtain a dose the drive wheel (10) rotates through a section of said predetermined angle and when push-button (40) is brought back to its initial position said drive wheel (10) rotates through the remainder of said predetermined angle.

10. Apparatus according to claim 1 also comprising a second metering ring (30) that is mounted to rotate around said rotation axis (1) and which is actuated to rotate by said first metering ring (20) each time that said first metering ring (20) completes a 360° rotation around said rotation axis (1).

* * * * *